United States Patent
Ghosh et al.

(10) Patent No.: US 10,975,002 B2
(45) Date of Patent: Apr. 13, 2021

(54) TOLUENE METHYLATION WITH TRANSALKYLATION OF HEAVY AROMATICS

(71) Applicant: SAUDI BASIC INDUSTRIES CORPORATION, Riyadh (SA)

(72) Inventors: Ashim Kumar Ghosh, Houston, TX (US); Mohamed Elbaccouch, Sugar Land, TX (US); Mohammad Shafiei, Sugar Land, TX (US); Murali Gopalakrishnan, Sugar Land, TX (US)

(73) Assignee: SAUDI BASIC INDUSTRIES CORPORATION, Riyadh (SA)

(*) Notice: Subject to any disclaimer, the term of this patent is extended or adjusted under 35 U.S.C. 154(b) by 468 days.

(21) Appl. No.: 15/689,452

(22) Filed: Aug. 29, 2017

(65) Prior Publication Data
US 2017/0362142 A1 Dec. 21, 2017

Related U.S. Application Data

(63) Continuation of application No. 14/022,643, filed on Sep. 10, 2013, now Pat. No. 9,783,462.

(51) Int. Cl.
*C07C 2/66* (2006.01)
*C07C 2/86* (2006.01)
*C07C 6/12* (2006.01)

(52) U.S. Cl.
CPC .............. *C07C 2/66* (2013.01); *C07C 2/864* (2013.01); *C07C 6/123* (2013.01); *C07C 2529/40* (2013.01)

(58) Field of Classification Search
CPC ........... C07C 2/66; C07C 2/864; C07C 6/123; C07C 2529/40
See application file for complete search history.

(56) References Cited

U.S. PATENT DOCUMENTS 3,702,886 A 11/1972 Argauer et al.
4,112,008 A 9/1978 Marcilly
(Continued)

FOREIGN PATENT DOCUMENTS

WO 0035836 A1 6/2000
WO 02062734 A1 8/2002
WO 2012154487 A2 11/2012

OTHER PUBLICATIONS

Exxon-Mobil; Printed Apr. 12, 2013; "TransPlus (heavy aromatics transalkylation)"; Taken from http://www.exxonmobilchemical.com/Chem-English/brands/transplus-heavy-aromatics-transalkylation.aspx?ln=productsservices; 1 page.
(Continued)

*Primary Examiner* — In Suk C Bullock
*Assistant Examiner* — Jason Y Chong
(74) *Attorney, Agent, or Firm* — Cantor Colburn LLP

(57) ABSTRACT

A method of producing a purified mixed xylene comprising: introducing toluene and methanol to an alkylation reactor; reacting the toluene and the methanol in the alkylation reactor to form a hydrocarbon stream comprising a first mixed xylene, wherein the alkylation reactor comprises an alkylation catalyst; separating the hydrocarbon stream into a toluene stream and a separated $C_{8+}$ stream; introducing the toluene stream to a transalkylation reactor with a transalkylation catalyst to produce a transalkylated stream comprising a second mixed xylene; adding the transalkylated stream to the hydrocarbon stream; and separating a $C_8$ product stream comprising the purified mixed xylene from the separated $C_{8+}$ stream.

10 Claims, 3 Drawing Sheets

(56) References Cited

U.S. PATENT DOCUMENTS

| | | | |
|---|---|---|---|
| 4,169,111 A | 9/1979 | Wight | |
| 5,030,787 A | 7/1991 | Absil et al. | |
| 5,763,720 A | 6/1998 | Buchanan et al. | |
| 5,942,651 A | 8/1999 | Beech, Jr. et al. | |
| 6,815,570 B1 | 11/2004 | Negiz et al. | |
| 7,060,864 B2 | 6/2006 | Ghosh et al. | |
| 7,084,318 B2 | 8/2006 | Ghosh et al. | |
| 7,105,713 B2 | 9/2006 | Ghosh et al. | |
| 7,196,237 B2 | 3/2007 | Ghosh et al. | |
| 7,244,869 B2 | 7/2007 | Ghosh et al. | |
| 7,279,608 B2 | 10/2007 | Ghosh et al. | |
| 7,285,511 B2 | 10/2007 | Ghosh et al. | |
| 7,304,194 B2 | 12/2007 | Ghosh et al. | |
| 7,368,410 B2 | 5/2008 | Ghosh et al. | |
| 7,399,727 B2 | 7/2008 | Ghosh et al. | |
| 7,446,069 B2 | 11/2008 | Ghosh et al. | |
| 7,507,685 B2 | 3/2009 | Ghosh et al. | |
| 7,560,608 B2 | 7/2009 | Ghosh et al. | |
| 7,576,026 B2 | 8/2009 | Ghosh et al. | |
| 7,625,793 B2 | 12/2009 | Calafut | |
| 7,629,498 B2 | 12/2009 | Brown et al. | |
| 7,662,737 B2 | 2/2010 | Ghosh et al. | |
| 7,674,942 B2 | 3/2010 | Ghosh et al. | |
| 7,713,898 B2 | 5/2010 | Ghosh et al. | |
| 8,062,987 B2 | 11/2011 | Ghosh et al. | |
| 8,115,041 B2 | 2/2012 | Ghosh et al. | |
| 2010/0305378 A1 | 12/2010 | Galloway, Jr. et al. | |
| 2011/0178354 A1 | 7/2011 | Negiz et al. | |
| 2012/0271071 A1 | 10/2012 | Haizmann et al. | |
| 2013/0267746 A1 | 10/2013 | Ding et al. | |

OTHER PUBLICATIONS

International Search Report for International Application No. PCT/EP2014/068588; International Filing Date Sep. 2, 2014; dated Nov. 24, 2014; 4 pages.

SK/KBR Technologies; Printed on Apr. 12, 2013; "Maximizing Benzene & Xylene Production"; Taken from http://www.kbr.com/technologies/Process-Technologies/Advanced-TransAlkylation/; 2 pages.

Written Opinion of the International Search Report for International Application No. PCT/EP2014/068588; International Filing Date Sep. 2, 2014; dated Nov. 24, 2014; 6 pages.

TOLUENE METHYLATION WITH TRANSALKYLATION OF HEAVY AROMATICS

CROSS-REFERENCE TO RELATED APPLICATION

This application is a continuation application of U.S. application Ser. No. 14/022,643 filed Sep. 10, 2013. The related application is incorporated herein in its entirety by reference.

TECHNICAL FIELD

The present disclosure relates generally to toluene methylation with transalkylation of heavy aromatics for preparing xylene product.

BACKGROUND

Descriptions of units, abbreviation, terminology, etc. used throughout the present disclosure are summarized in Table 1.

Aromatic compounds can be alkylated to form different alkylated aromatic products. One that has particular value is para-xylene (also referred to as p-xylene). Para-xylene is a valuable substituted aromatic compound due to its great demand of approximately 30 million metric tons per year for further oxidation to terephthalic acid, a major component in forming polyester fibers and resins. Commercially, para-xylene is generally produced by one of two methods. The first and most prominent, from which more than about 80% of the para-xylene is derived, involves hydrotreating of naphtha (catalytic reforming) and/or steam cracking of naphtha or gas oil. The second method, from which more than about 15% of the para-xylene is derived, involves toluene disproportionation (TDP) to produce benzene and mixed xylene (it is noted that mixed xylene comprises o-, m-, and p-xylene), where the p-xylene is generally present in an amount of about 20 to 25% based on the total xylene. In a shape selective toluene disproportionation (also known as STDP) p-xylene content in mixed xylene can be greater than 80%, specifically, greater than or equal to 90%, more specifically, greater than or equal to 95%. Para-xylene can then be further separated from mixed xylene produced by catalytic reforming or naphtha cracking or toluene disproportionation.

Alkylation of toluene with methanol, which is also known as toluene methylation, has been used in laboratory studies to produce mixed xylene. Generally, a thermodynamic equilibrium mixture of o-, m-, and p-xylene can be formed from the methylation of toluene, as is illustrated by the following reaction:

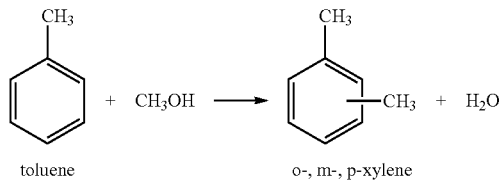

When a shape selective catalyst, such as a modified ZSM-5 zeolite catalyst is used for toluene methylation, the reaction can produce mixed xylene with the p-xylene isomer being greater than or equal to 80%. However, the byproducts of toluene methylation, including $C_{9+}$ aromatics are produced due to secondary alkylation of xylene and alkylation of toluene with $C_{2+}$ compounds. Such $C_{9+}$ aromatic byproducts are less valuable than the xylene and such byproduct formation can make the toluene methylation commercially unattractive. Furthermore, there are a number of technical hurdles (e.g., catalyst deactivation, low methanol selectivity) for toluene alkylation to be commercially attractive and an improved method of preparation of mixed xylene is desirable.

SUMMARY

Disclosed herein are methods of producing mixed xylene.

In an embodiment, a method of producing a purified mixed xylene comprises: introducing toluene and methanol to an alkylation reactor; reacting the toluene and the methanol in the alkylation reactor to form a hydrocarbon stream comprising a first mixed xylene, wherein the alkylation reactor comprises an alkylation catalyst; separating the hydrocarbon stream into a toluene stream and a separated $C_{8+}$ stream; introducing the toluene stream to a transalkylation reactor with a transalkylation catalyst to produce a transalkylated stream comprising a second mixed xylene; adding the transalkylated stream to the hydrocarbon stream; and separating a $C_8$ product stream comprising the purified mixed xylene from the separated $C_{8+}$ stream.

The foregoing and other features of the present disclosure will be more readily apparent from the following detailed description and drawings of the illustrative embodiments.

BRIEF DESCRIPTION OF THE DRAWINGS

Refer now to the figures, which are exemplary embodiments, and wherein the like elements are numbered alike.

DETAILED DESCRIPTION

TABLE 1

Figure 1:
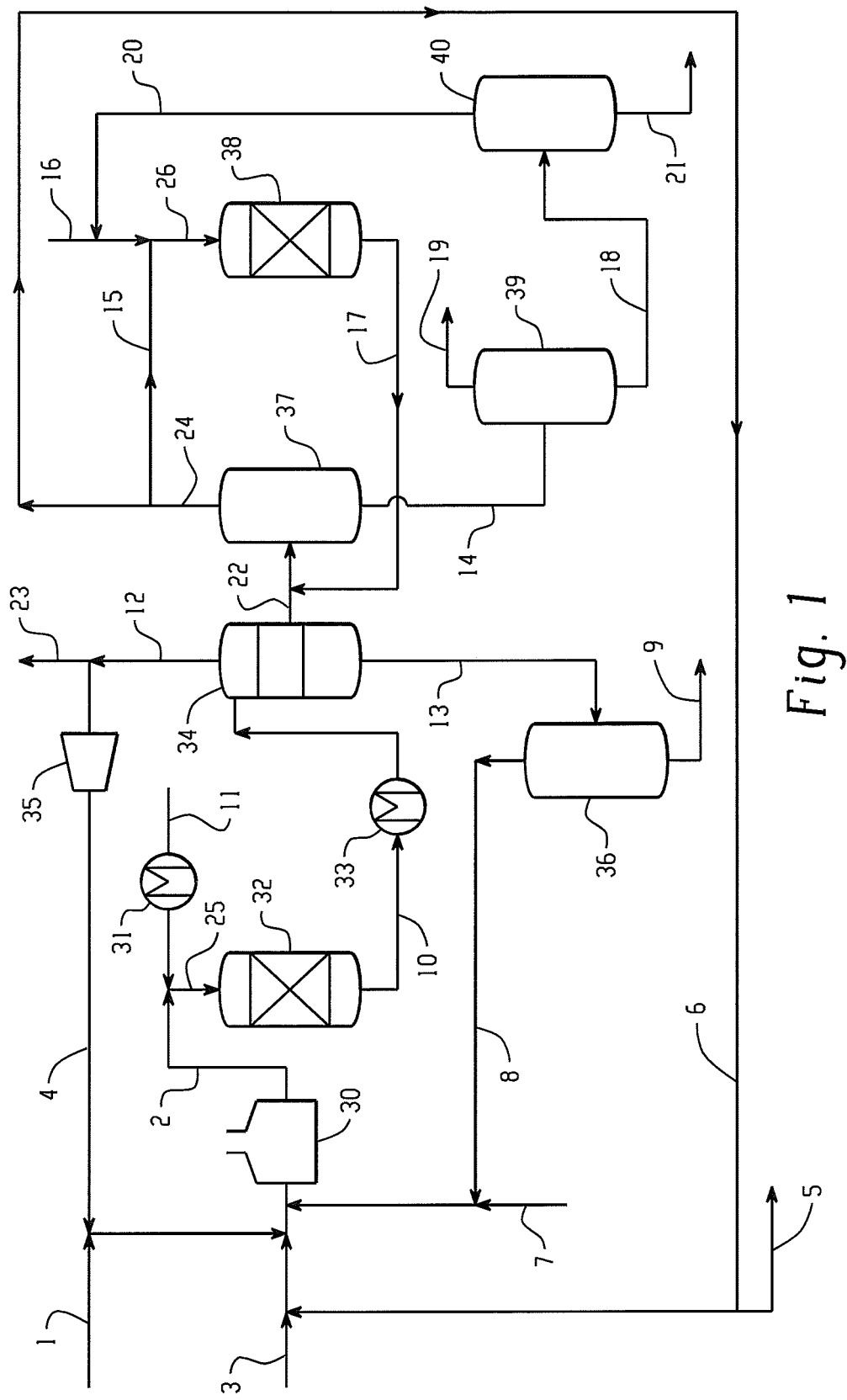
FIG. 1 is an illustration of a method of producing mixed xylene.

| Abbreviation | Description |
|---|---|
| $C_8$ | molecule(s) with 8 carbon atoms |
| $C_{8+}$ | molecule(s) with 8 or more carbon atoms |
| $C_9$ | molecule(s) with 9 carbon atoms |
| $C_{9+}$ | molecule(s) with 9 or more carbon atoms |
| $C_{10+}$ | molecule(s) with 10 or more carbon atoms |
| $ | US dollars |
| p-xylene | para-xylene |
| m-xylene | meta-xylene |
| o-xylene | ortho-xylene |
| mixed xylene | mixture of o-, m- and p-xylene |
| xylene | mixture of o-, m- and p-xylene |
| % | percent |
| Å | angstrom |
| ° C. | degrees Celsius |
| cm | centimeter |
| cc/g | cubic centimeters per gram |
| GHSV | gas hourly space velocity |
| h | hour |
| HOS | hours on stream |
| kg/h | kilogram/hour |
| kPa | kilo Pascal |
| L | liters |
| MM | million |

TABLE 1-continued

| Abbreviation | Description |
| --- | --- |
| m²/g | meters squared per gram |
| mol % | mole percent |
| MPa | mega Pascal |
| ppm | parts per million by weight |
| psig | pounds per square inch gauge |
| SAR | silica to alumina mole ratio |
| sccm | standard cubic centimeter per minute |
| TA | transalkylation |
| TM | toluene methylation |
| WHSV | weight hourly space velocity |
| wt % | weight percent |

Commercial production of mixed xylene (from which p-xylene can be separated) via toluene alkylation can be unattractive due to a number of technical hurdles, for example, due to byproduction of less valuable $C_{9+}$ compounds (i.e., aromatic compounds having 9 or more carbon atoms, also referred to herein as $C_{9+}$ aromatics). Examples of $C_9$ aromatic compounds include trimethylbenzene (TMB) (e.g., one or more of 1,2,3-trimethylbenzene, 1,2,4-trimethylbenzene, and 1,3,5-trimethylbenzene), ethyltoluene (e.g., one or more of 2-ethyltoluene, 3-ethyltoluene, and 4-ethyltoluene), n-propylbenzene, and so on. Examples of $C_{10}$ aromatics include isomers of tetramethylbenzene and the like. Also, the toluene feedstock can contain $C_{9+}$ aromatics that require additional processing (e.g., separation, etc.). The Applicants therefore developed a commercially attractive process by which mixed xylene can be prepared by toluene alkylation. The process includes a transalkylation process of the $C_{9+}$ compounds with unconverted toluene to produce mixed xylene. Specifically, the process involves alkylating toluene with an alkylating agent in an alkylation reactor containing an alkylation catalyst that can be a shape selective catalyst; separating out water, unconverted alkylating agent, and oxygenates from the unconverted toluene and alkylated products; and transalkylating (also referred to as disproportionating) any $C_{9+}$ aromatics with at least a portion of the unconverted toluene in a transalkylation reactor containing a transalkylation catalyst. The $C_{9+}$ aromatics can arise from, for example, formation as byproduct in the alkylation reactor and/or impurities in toluene feedstock or can be supplied from another source.

The present process changes the paradigm for producing the xylene, particularly by alkylation of toluene. Previously, focus has been on improving product selectivity at the expense of toluene conversion; minimizing the production of less valuable $C_{9+}$ aromatic byproducts. As such, a catalyst with selectivity for mixed xylene of, for example, greater than 95% (based on toluene conversion) was needed for a commercially viable toluene methylation process.

The present process, however, does not negatively impact the mixed xylene production from the production of heavy aromatics, such as $C_{9+}$ aromatics, in the alkylation reactor, or the presence of $C_{9+}$ aromatics as toluene feed impurities. Actually, the process can benefit from the cheaper $C_{9+}$ aromatics present in alkylation feed or its production in the alkylation reactor since the product selectivity is less stringent. A selectivity for mixed xylene of greater than or equal to 70 mole percent (mol %), specifically, greater than or equal to 80 mol %, more specifically, greater than or equal to 85 mol %, even more specifically, greater than or equal to 90 mol %, still more specifically, greater than or equal to 95 mol % resulting in a selectivity for $C_{9+}$ aromatics less than or equal to 30 mol %, specifically, less than or equal to 20 mol %, more specifically, less than or equal to 15 mol %, even more specifically, less than or equal to 10 mol %, still more specifically, less than or equal to 5 mol % is acceptable. Actually, this process even allows a selectivity for mixed xylene of less than or equal to 75 mol %. Therefore, the toluene conversion can be significantly increased by using a more active catalyst, which can be less selective for alkylation reaction or by using severe alkylation conditions. Furthermore, since the $C_{9+}$ aromatics are subsequently reacted with toluene to produce additional mixed xylene, the $C_{9+}$ aromatic products and any that may be present in the toluene feedstock are actually beneficial in the present process. This is particularly beneficial when the toluene feedstock contains $C_{9+}$ aromatics as impurities that remain unconverted and are present in the toluene methylation reactor product stream. A toluene feedstock containing greater than or equal to 10 wt %, specifically, greater than or equal to 15 wt %, more specifically, greater than or equal to 20 wt %, still more specifically, greater than or equal to 30 wt % $C_{9+}$ aromatics (based upon a total weight of the toluene feedstock) can be now suitable for toluene methylation. Hence, the toluene feed stream can contain 0 to greater than or equal to 30 wt % $C_{9+}$ aromatics (e.g., greater than or equal to 10 wt % $C_{9+}$ aromatics, etc.).

As mentioned above, it was found that in the present method of producing mixed xylene that the alkylation catalyst could comprise a low selective alkylation catalyst, with a mixed xylene selectivity of less than or equal to 95 mol %, specifically, less than or equal to 85 mol %, more specifically, less than or equal to 70 mol % to achieve a high toluene conversion to mixed xylene. Specifically, the present method of producing xylene using a shape selective alkylation catalyst can result in greater than or equal to 1.09 g mixed xylene per gram of toluene converted at 95 mol % selectivity and/or less than or equal to 0.07 g of $C_{9+}$ aromatics per gram of toluene converted at 95 mol % selectivity. The present method of producing xylene using a shape selective alkylation catalyst can result in greater than or equal to 0.92 g mixed xylene per gram of toluene converted at 80 mol % selectivity and/or less than or equal to 0.26 g $C_{9+}$ aromatics per gram of toluene converted at 80 mol % selectivity. The present method can result in greater than or equal to 0.81 g mixed xylene per gram of toluene converted at 70 mol % selectivity and/or 0.39 g $C_{9+}$ aromatics per gram of toluene converted at 70 mol % selectivity. The present method can result in toluene conversion of greater than or equal to 20 wt % producing greater than or equal to 0.05 g of $C_{9+}$ aromatics per gram of toluene converted.

Further, the toluene methylation catalyst can comprise a shape selective catalyst with p-xylene selectivity (mol % p-xylene in mixed xylene) of greater than or equal to 80 mol %, specifically, greater than or equal to 90 mol %, more specifically, greater than or equal to 95 mol %. Such a high p-xylene concentration in the mixed xylene can be economically attractive for its separation.

The present method of making mixed xylene comprises a toluene alkylation followed by transalkylation of at least a portion of the unreacted toluene from the toluene alkylation with $C_{9+}$ aromatics. The $C_{9+}$ aromatics can be formed as byproduct in toluene alkylation reactor and/or obtained from a different source. The $C_{9+}$ aromatics can be present as impurities in the alkylation feed and/or can be formed as byproduct in the alkylation reactor. Additional $C_{9+}$ can also be imported from other sources.

Toluene alkylation comprises adding toluene (that comprises fresh toluene and optionally recycled toluene) and an alkylating agent such as methanol to an alkylation reactor that comprises an alkylation catalyst. The toluene feed can contain greater than or equal to 1 wt %, or greater than or equal to 5 wt %, specifically, greater than or equal to 10 wt %, more specifically, greater than or equal to 20 wt %, even more specifically, greater than or equal to 30 wt % heavy aromatics such as $C_{9+}$, based upon a total weight of the toluene feed. The toluene feed can optionally contain one or both of water (for example as steam) and an inert gas such as hydrogen. The alkylation reaction can occur at an elevated temperature, for example, greater than or equal to 400° C., specifically, 500 to 650° C., more specifically, 550 to 600° C. The stream leaving the alkylation reactor can comprise unreacted toluene, unreacted methanol, hydrogen, methane, ethane, ethylene, water, $C_8$ compounds (such as o-, m-, and p-xylene), $C_9$ compounds (such as trimethylbenzene, ethyltoluene (methylethylbenzene), propylbenzene, and the like), $C_{10+}$ compounds, or a combination comprising one or more of the foregoing.

The transalkylation reaction involves reacting $C_{9+}$ aromatics with toluene (e.g., unreacted toluene from the toluene alkylation reaction and/or fresh toluene). The transalkylation reaction can occur at a temperature of greater than or equal to 100° C., specifically, 200 to 700° C., more specifically, 300 to 600° C. Likewise, the temperature of the transalkylation reaction can be increased with time. The transalkylation reaction can occur at a pressure of 100 kPa to 10 MPa, specifically, 0.5 to 5 MPa. The transalkylation reaction can occur at a WHSV based on the combined feed to the transalkylation reactor of 0.1 to 30 h$^{-1}$, specifically, 0.5 to 20 h$^{-1}$, more specifically, 1 to 5 h$^{-1}$, where WHSV is the weight of the feed charged per hour to the reactor divided by the weight of the catalyst.

Specifically, transalkylation reaction under the above conditions results in a decrease of toluene and $C_{9+}$ aromatics and increase of xylene product. Specifically, the decrease of toluene and $C_{9+}$ aromatics can be greater than or equal to 5%, specifically, greater than or equal to 10%, more specifically, greater than or equal to 20%, even more specifically, greater than or equal to 30%. Consequently, by combining toluene methylation with transalkylation two moles of xylene can be produced from one mole of toluene and one mole of $C_{9+}$ aromatics.

FIG. 1 shows an illustration of a method of making mixed xylene. Specifically, hydrogen stream 1, which can be optionally combined with hydrogen recycle stream 4; toluene stream 3, which can be combined with an optional toluene recycle stream 6; and water stream 7, which can be combined with optional water recycle stream 8 are introduced to heater 30. Toluene stream 3 can comprise 0 to 30 wt %, specifically, 1 to 30 wt %, more specifically, 3 to 30 wt %, even more specifically, 10 to 30 wt % of $C_{9+}$ aromatics based on the total weight of the toluene stream. Stream 8 can contain methanol depending on methanol conversion in alkylation reactor. The heater 30 can increase the temperature of the mixture to greater than or equal to 500° C., specifically, 500 to 650° C., more specifically, 550 to 600° C. Heated stream 2 can be combined with a methanol stream 11 that can be heated to a temperature of greater than or equal to 500° C., specifically, 500 to 650° C., more specifically, 550 to 600° C. in heater 31. It is noted that heater 31 could instead be, for example, a heat-exchanger. The heated stream 2 and methanol stream 11 can be introduced as separate streams or can be combined and then introduced as alkylation stream 25 to toluene alkylation reactor 32 that comprises a methylation catalyst to produce alkylated stream 10. Alkylated stream 10 can comprise unreacted toluene, unreacted methanol, hydrogen, methane, ethane, ethylene, water, $C_8$ compounds (such as o-, m-, and p-xylene), $C_9$ compounds (such as trimethylbenzene, ethyltoluene, methylethylbenzene, propylbenzene, and the like), $C_{10+}$ compounds, or a combination comprising one or more of the foregoing. Alkylated stream 10 can be cooled in cooler 33 to a temperature of less than or equal to 50° C., specifically, 2 to 40° C.

The cooled alkylated stream can then be added to a liquid-liquid-vapor (LLV) separator 34 that functions to separate the cooled alkylated stream 10 into vapor stream 12, hydrocarbon stream 22, and aqueous stream 13. Vapor stream 12 can comprise hydrogen, light hydrocarbons such as methane, ethylene, propylene, and so on, and can be removed from the system, recycled, or both. Recycling all or a portion of the vapor stream 12 can recover hydrogen. For example, a first portion of vapor stream 12 can optionally be released as vapor purge 23 and the remaining portion of vapor stream 12 can be introduced to a compressor 35 for use as hydrogen recycle stream 4. The vapor purge 23 can be used to help maintain the olefin concentration. Aqueous stream 13 that can comprise water and methanol can be introduced to methanol column 36, which can separate the aqueous stream 13 into recycle water stream 8, and waste water stream 9 that can comprise 0 to 400 ppm, specifically, 2 to 200 ppm of methanol. Recycle water stream 8 can contain 0 to 10 wt % methanol. Hydrocarbon stream 22 that can comprise unconverted toluene, o-xylene, m-xylene, p-xylene, $C_{9+}$ compounds, and the like, or a combination comprising one or more of the foregoing, can be introduced to toluene separation column 37. The toluene separation column 37 can separate the hydrocarbon stream 22 into separated $C_{8+}$ stream 14 and toluene stream 24, where a first portion of toluene stream 24 can be used as a toluene recycle stream 6. A portion of toluene recycle stream 6 can be removed via benzene purge 5. Likewise, all or a portion of the toluene stream 24 as separated toluene stream 15 can be combined with $C_9$ stream 20 and optionally with $C_{9+}$ stream 16 and introduced to transalkylation reactor 38. The transalkylation reactor that can comprise a transalkylation catalyst, produces transalkylated stream 17. Transalkylated stream 17 can be combined with hydrocarbon stream 22 and can be added to toluene separation column 37 in order to introduce more xylene into said column.

Separated $C_{8+}$ stream 14 can be introduced to xylene separation column 39 that can separate said stream into separated $C_{9+}$ stream 18 and $C_8$ product stream 19. Product stream 19 can comprise purified mixed xylene in an amount of greater than or equal to 85 wt % p-xylene based on the total amount of mixed xylene. Product stream 19, containing a high concentration of p-xylene in mixed xylene, is further processed to separate p-xylene by, for example, adsorption or crystallization technology. Separated $C_{9+}$ stream 18 can be introduced to $C_9$ separation column 40 to separate the stream into $C_9$ stream 20 and $C_{10+}$ stream 21.

Toluene alkylation occurs in the alkylation reactor in the presence of an alkylation catalyst. The alkylation catalyst can be any catalyst capable of performing the alkylation of toluene producing mixed xylene and having a selectivity of greater than or equal to 70 mol %, specifically, greater than or equal to 80 mol % and, an activity of toluene conversion greater than or equal to 20%. Herein, selectivity refers to mixed xylene selectivity and refers to percent mixed xylene in total aromatics formed.

The alkylation catalyst can comprise a high selectivity alkylation catalyst, where high selectivity refers to a mixed xylene selectivity of greater than or equal to 70 mol %, specifically, greater than or equal to 80 mol %, more specifically, greater than or equal to 90 mol %. By varying the alkylation catalyst or alkylation conditions such as increasing partial pressure of alkylating agent (e.g., increasing methanol/toluene ratio) the toluene conversion can be increased. Such an increase of toluene conversion can result in an increase of $C_{9+}$ aromatics formation and ultimately in a decrease in mixed xylene selectivity.

The alkylation catalyst can be a zeolite catalyst. The zeolite can be any of a number of zeolites, where zeolites are crystalline aluminosilicates with a three-dimensional framework containing silica ($SiO_4$) and alumina ($AlO_4$) tetrahedra, and can be naturally occurring or synthesized. In general, the zeolite framework contains channels and interconnected voids or pores, which can be occupied by cations and water molecules. Depending on the size and geometry of the pores and channels, zeolites can be classified as small, medium, or large pore zeolites, and also as one, two, or three-dimensional pore structure zeolites.

The zeolite can be from a family of pentasil zeolites that contain five membered ring units or pentasil units in the framework structure. Such zeolites include ZSM-5, ZSM-11, ZSM-23, ferrierite, mordenite, and so on. Silicalite, which contains an isotypic framework of ZSM-5 can also be included. Specifically, the zeolite can be a pentasil zeolite, which contains 10-membered ring pore openings in the structure. Zeolites with the 10-membered pore openings are also known as medium pore zeolites. Examples of such pentasil zeolite containing 10-membered ring pore openings or medium pore are ZSM-5, ZSM-11, silicalite, etc.

The zeolite can be ZSM-5 or MFI (International Zeolite Association nomenclature of ZSM-5). The ZSM-5 zeolite has two-dimensional pore structure with straight channels (5.4 Å×5.6 Å), which are intersected by sinusoidal channels (5.1 Å×5.7 Å) with a maximum diameter of 9 Å at the intersection. The ZSM-5 zeolite catalysts and their preparation are described, for example, in U.S. Pat. No. 3,702,886. Such ZSM-5 zeolites are aluminosilicates that contain both silicon and aluminum in the crystalline structure. ZSM-11 is another pentasil aluminosilicate zeolite that is similar to ZSM-5.

The starting zeolite can be an $NH_4^+$ or $H^+$ form. It can optionally contain up to trace levels of other cations (wherein a trace level is less than or equal to 0.5 wt % based upon the total weight of the zeolite).

The alkylation catalyst can be a shape selective zeolite catalyst that produces para-xylene at significantly greater, for example greater than or equal to 300% greater, than equilibrium concentration of p-xylene in the mixed xylene by reaction of toluene and methanol, hereinafter called toluene methylation. Such shape selective catalysts are often zeolite catalysts, particularly medium pore zeolites, such as ZSM-5 zeolite. Herein, the term "shape selective catalyst" also refers as p-xylene selective catalyst. Non-limiting examples of suitable p-xylene selective catalysts, can include those described in U.S. Pat. Nos. 7,060,864; 7,084,318; 7,105,713; 7,196,237; 7,244,869; 7,279,608; 7,285,511; 7,304,194; 7,368,410; 7,399,727; 7,446,069; 7,507,685; 7,560,608; 7,576,026; 7,629,498; 7,625,793; 7,662,737; 7,674,942; 7,713,898; 8,062,987; and 8,115,041.

The p-xylene selective catalyst can be a phosphorus-containing zeolite, which can be a medium pore zeolite such as a ZSM-5 zeolite, that is bound with an inorganic binder and has at least two $^{31}P$ MAS NMR peaks with at maxima at 0 to −55 ppm, with at least one $^{31}P$ MAS NMR peak having a maximum at −40 to −50 ppm. Such catalysts, their preparation, and use are described in detail in U.S. Pat. Nos. 7,368,410; 7,507,685; and 7,674,942.

The phosphorus-containing zeolite can be prepared by treating the zeolite with a phosphorus-containing compound. The zeolite can be a medium pore zeolite, such as a ZSM-5 zeolite. The zeolite can include those having a $SiO_2/Al_2O_3$ molar ratio of greater than or equal to 25, specifically, greater than or equal to 50, more specifically, greater than or equal to 100, even more specifically, greater than or equal to 200, still more specifically 200 to 500, prior to modification. The starting ZSM-5 zeolite can be an $NH_4^+$ or $H^+$ form and can contain traces of other cations.

The phosphorus-containing compounds can include, but are not limited to, phosphonic, phosphinous, phosphorus and phosphoric acids, salts and esters of such acids and phosphorous halides. For example, phosphoric acid ($H_3PO_4$), ammonium dihydrogen phosphate ($NH_4H_2PO_4$) and ammonium hydrogen phosphate (($NH_4)_2HPO_4$) can be used as the phosphorus-containing compound to provide a catalyst for toluene methylation with shape selective properties to provide increased p-xylene selectivity. Such modified catalysts can contain phosphorus (P) in an amount of 0.01 to 0.15 g P/g zeolite, more specifically, 0.02 to 0.13 g P/g zeolite, more specifically, 0.07 g P/g zeolite to 0.12 g P/g zeolite, and still more specifically 0.09 g P/g zeolite to 0.11 g P/g zeolite. After phosphorus treatment, the phosphorus-treated zeolite can be dried.

The phosphorus treatment of the zeolite can be carried out by various techniques, such as slurry evaporation, wet incipient methods, and/or spray-dry methods. In slurry evaporation, phosphorus can be incorporated into the zeolite by preparing a slurry of the zeolite and an aqueous solution of the phosphorus compound. Heating of the slurry can be used to facilitate treatment of the zeolite and to evaporate liquids. Heating of the slurry can occur at temperatures of greater than or equal to 25° C., specifically, 70 to 100° C. The slurry can also be stirred or agitated during this step to ensure uniform treatment.

The evaporation of the liquid from the zeolite slurry can be alternatively, or additionally, achieved by using a spray-dry technique. In the wet incipient method, an aqueous solution of the phosphorus compound is added, such as by spraying, to the dry zeolite without forming a slurry. The dry zeolite, which can be initially in the form of a powder, can be mixed with the phosphorus compound or its aqueous solution. Water can be added to the mixture of zeolite powder and phosphorus containing compound or its solution to facilitate uniform interaction between them.

The phosphorus treated zeolite can be calcined using a temperature profile, e.g., with a maximum temperature of 400 to 700° C. Optionally, the phosphorus zeolite can be heated at a temperature of 300° C. or higher prior to binding and then the treated zeolite can be bound with a suitable binder, as described, for example, in U.S. Pat. No. 7,368,410. Calcining can take place over time, typically several minutes to one hour or more, specifically, 30 minutes to 10 hours, more specifically, 30 minutes to 5 hours. Calcining can take place for greater than or equal to 30 minutes, specifically, greater than or equal to 5 hours, more specifically, greater than or equal to 10 hours. Calcining can also take place by gradually increasing the temperature over time.

In certain embodiments, the p-xylene selective catalyst is a P-modified ZSM-5 zeolite contains an insignificant amount of tetrahedral/structural Al in the zeolite framework showing a weak $^{27}Al$ MAS NMR peak at around 50 ppm, but the catalyst contains "debris" or extra-framework aluminum (EFWAl) inside the zeolite pores and channels showing a strong $^{27}Al$ MAS NMR peak at around −14 ppm.

The ratio of the framework aluminum over extra framework aluminum for the P-treated zeolite catalyst can be 0.12 to 0.25 (for example, in U.S. Pat. No. 7,285,511).

After the heating step, as discussed above, the phosphorus-modified zeolite can then be bound with a suitable binder. Suitable binder materials can include inorganic oxide materials. Examples of such materials include alumina, clay, aluminum phosphate, silica and silica-alumina. In particular, a binder of alumina, silica-alumina or clay or their combinations are particularly useful. The bound catalyst can contain from 1 to 99 wt %, specifically, 10 to 50 wt % binder based on the total weight of bound catalyst.

To form the bound catalyst, the binder material can be combined with the phosphorus-modified zeolite to form an extrudable mixture. After binding, the phosphorus-modified zeolite bound with the binder can be calcined or heated at a temperature of greater than or equal to 400° C. or higher, more specifically, 450 to 700° C. Such heating can be carried out for 0.5 hours or more to form the bound catalyst. It has been discovered that heating the P-treated ZSM-5 at a temperature of greater than or equal to 300° C. and then binding the zeolite with a suitable binder, as described herein, can result in the bound zeolite exhibiting multiple P-species, as shown by $^{31}$P MAS NMR peaks.

The catalyst can be activated by first drying at a temperature of 100 to 250° C. for 0.5 to 3 hours under flow of an inert gas such as $H_2$ of 50 to 500 sccm. The activation can occur at greater than or equal to atmospheric pressure, specifically, at greater than or equal to 50 psig, more specifically, at greater than or equal to 100 psig.

Optionally, the catalyst can be steamed prior to use for the catalytic reactions. The catalyst can be steamed at a temperature of 200 to 600° C., specifically 200 to 400° C., e.g., for a period of more than 0.5, e.g., a period of 1 to 10 h, before using the catalyst in any reaction. The steaming can be carried out in-situ or ex-situ of the reactor. The catalyst can be steamed at mild temperatures. Methods for steaming at mild temperatures are described, for example, in U.S. Pat. No. 7,304,194.

Furthermore, the shape selective alkylation catalyst can contain a hydrogenating metal such as platinum, nickel, palladium, and the like. The resulting zeolite catalyst can have shape selective properties showing greater than or equal to 80 mol %, specifically, greater than or equal to 90 mol %, more specifically, greater than or equal to 95 mol % para-xylene selectivity for toluene methylation reaction. Such a catalyst shows stable catalyst performance showing little or no decline in toluene conversion with reaction time.

The hydrogenating metal containing shape selective catalyst can require catalyst activation step including first drying at a temperature of 100 to 250° C. for 0.5 to 3 hours under flow of a reducing gas of 50 to 500 sccm and then heating at a temperature of 250 to 600° C. for 0.5 to 5 hours under flow of a reducing gas of 50 to 500 sccm. The activation can occur at greater than or equal to atmospheric pressure, specifically, at greater than or equal to 50 psig, more specifically, at greater than or equal to 100 psig. Optionally, the catalyst can be steamed prior to use for the catalytic reactions as described earlier.

Transalkylation of heavy aromatics such as $C_9$ aromatics with toluene occurs in a transalkylation reactor or in a reaction zone in the presence of a transalkylation catalyst under transalkylation reaction conditions. The transalkylation catalyst can be any catalyst that can successfully convert the aromatics to $C_8$ aromatics, for example xylene. The transalkylation catalyst can comprise a metal component and an acidic component. The metal component can be any metal that has a hydrogenation functionality, and it can be any noble metal or combinations of other metals. The acidic component can be non-zeolite or zeolite. Zeolite can be any zeolite including crystalline aluminosilicate such as zeolite beta, zeolite Y, mordenite, and the like. An example of a transalkylation catalyst is a mordenite zeolite having a silica alumina (molar) ratio (SAR) of greater than or equal to 40:1 that can be prepared by dealuminating the zeolite by steaming or acid treatment of mordenite having an initial SAR of 12:1 to 30:1 and optionally a metal component (such as copper, silver, and zirconium. The transalkylation catalyst can comprise a binder or matrix. Examples include inorganic oxides such as alumina, magnesia, zirconia, chromia, titania, boria, thoria, phosphate, zinc oxide, silica, and the like.

The transalkylation catalyst can comprise a metal component that has hydrogenation function such as a Groups 8-10 metal, specifically, a Group 10 metal that can be deposited on the catalyst via, for example, impregnation. The metal component can be present for example as a metal oxide, a metal sulfide, a metal halide, a metal oxyhalide, or as the elemental metal. The metal component can be present in a catalytically active amount, for example, the transalkylation catalyst can comprise 0.01 to 10 wt %, specifically, 0.01 to 2 wt % based on the total weight of the catalyst. Likewise, the transalkylation catalyst can comprise a metal component that can be incorporated as a framework or a non-framework element such as tin, germanium, lead, indium, and the like. These elements can be present in a catalytically active amount, where the transalkylation catalyst can comprise, for example, 0.01 to 10 wt %, specifically, 0.01 to 2 wt % based on the total weight of the catalyst.

The transalkylation catalyst can be formed into a shape. For example the transalkylation catalyst can be formed into a cylinder (such as a cylinder with a diameter of less than or equal to 0.08 cm and an aspect ratio of less than or equal to 3, where the aspect ratio is defined by the height divided by the diameter) or a shape having a tri-lobal or three-leaf clover type cross section, with for example a maximum diameter as defined by circumscribing an effective circle around the entire tri-lobal shape of less than or equal to 0.16 cm.

The following examples are provided to illustrate the method of producing mixed xylene. The examples are merely illustrative and are not intended to limit devices made in accordance with the disclosure to the materials, conditions, or process parameters set forth therein.

EXAMPLES

Example 1: Catalyst Preparation

A P-modified ZSM-5 catalyst was prepared using a $NH_4$-ZSM-5 zeolite powder having a $SiO_2/Al_2O_3$ mole ratio of 282 by treating with P-containing compound ($H_3PO_4$) and then heating to a maximum temperature of about 550° C. to form a P/ZSM-5 zeolite powder catalyst (A). The powder catalyst (A) was bound with 20 wt % alumina as binder and extruded to make ¹⁄₁₆-inch cylindrical shaped extruded catalyst. The catalyst was calcined or heated at a maximum temperature of about 550° C. in air for about five hours (Extruded Catalyst A).

A second P-modified ZSM-5 catalyst was prepared by using $NH_4$—ZSM-5 zeolite powder having a $SiO_2/Al_2O_3$ mole ratio of 302 by treating with P-containing compound ($H_3PO_4$) and then heating to a maximum temperature of about 550° C. to form a P/ZSM-5 zeolite powder catalyst (B). The powder catalyst (B) was bound with about 20 wt % alumina as binder and extruded to make 1/16-inch cylindrical shaped extruded catalyst. The catalyst was calcined or heated at a maximum temperature of about 550° C. in air for about five hours (Extruded Catalyst B).

Analyses of powder and extruded catalysts A and B are shown in Table 2. BET surface area (BET SA) and total pore volume (PV) as determined by $N_2$ adsorption technique, for both Catalysts A and B are also shown in Table 2.

TABLE 2

| Catalyst | Elemental Analysis, wt % | | | $N_2$ Adsorption | |
|---|---|---|---|---|---|
| | Si | Al | P | BET SA, $m^2/g$ | PV, cc/g |
| Powder Catalyst A | 36.3 | 0.28 | 8.5 | 168 | 0.12 |
| Extruded Catalyst A | 29.6 | 9.8 | 7.1 | 205 | 0.16 |
| Powder Catalyst B | 35.7 | 0.31 | 8.7 | 199 | 0.13 |
| Extruded Catalyst B | 29.3 | 9.9 | 7.0 | 200 | 0.16 |

Example 2: Toluene Methylation Over Extruded Catalyst A

Extruded Catalyst A was used in a toluene methylation reaction with a reactor unit containing three reactors in series. In each of the reactors, 40 g of 1/16-inch extruded catalyst was loaded. The catalyst was dried at 200° C. under hydrogen flow (1500 sccm) for at least one hour. The catalyst was steamed by introducing water vapor (6.5 g/h) with a carrier gas of $H_2$ (1500 sccm) at 200° C. overnight. Reaction feed was introduced as follows: hydrogen rate at 3000 sccm, toluene at 90 g/h, steam at 18.5 g/h, and methanol at 6.8 g/h to the first reactor. Additional methanol feed was added to second and third reactors at 5.9 g/h and 4.8 g/h, respectively. The inlet pressure for all three reactors was adjusted to 20 psig. Catalyst bed temperature was adjusted to 530° C., 541° C., and 551° C. for first, second, and third reactors, respectively. The catalyst testing continued for more than 140 days with multiple catalyst regenerations. The method of catalyst regeneration is described, for example, in U.S. Pat. No. 8,115,041. After each catalyst regeneration, alkylation reaction conditions were different than those with the fresh load of catalyst. The reaction conditions, averaged toluene conversion, and reaction products of mixed xylene, p-xylene, and $C_{9+}$ aromatics for fresh and regenerated catalyst are shown in Table 3, where "catalyst regen" refers to regenerated catalyst.

TABLE 3

| Extruded Catalyst A | | | | | | | Product, g per g toluene converted | | |
|---|---|---|---|---|---|---|---|---|---|
| Regeneration No. | Run days | T, ° C. | P, psig | Tol/ MeOH | WHSV, $h^{-1}$ | $X_{tol}$ | Mixed xylene | p-xylene | $C_{9+}$ Aromatics |
| Fresh Catalyst | 1-22 | 500-550 | 20 | 1.7 | 0.9 | 33.6 | 1.09 | 0.96 | 0.04 |
| Regen 1 | 24-35 | 500-550 | 20 | 1.7 | 0.9 | 34.4 | 1.10 | 0.95 | 0.05 |
| Regen 2 | 40-55 | 500-550 | 20 | 1.7 | 0.9 | 34.9 | 1.10 | 0.99 | 0.06 |
| Regen 3 | 59-76 | 500-550 | 20 | 1.7 | 0.9 | 35.5 | 1.09 | 0.98 | 0.06 |
| Regen 4 | 84-90 | 500-550 | 20 | 1.7 | 0.9 | 32.0 | 1.11 | 1.03 | 0.05 |
| Regen 5 | 94-111 | 500-550 | 20 | 1.7 | 0.9 | 36.2 | 1.09 | 0.97 | 0.06 |
| Regen 6 | 115-132 | 500-550 | 20 | 1.7 | 0.9 | 35.6 | 1.09 | 0.97 | 0.06 |
| Regen 7 | 138-143 | 500-550 | 20 | 1.7 | 0.9 | 36.2 | 1.09 | 0.96 | 0.06 |

All data presented in table are averaged during the period.

Figure 2:
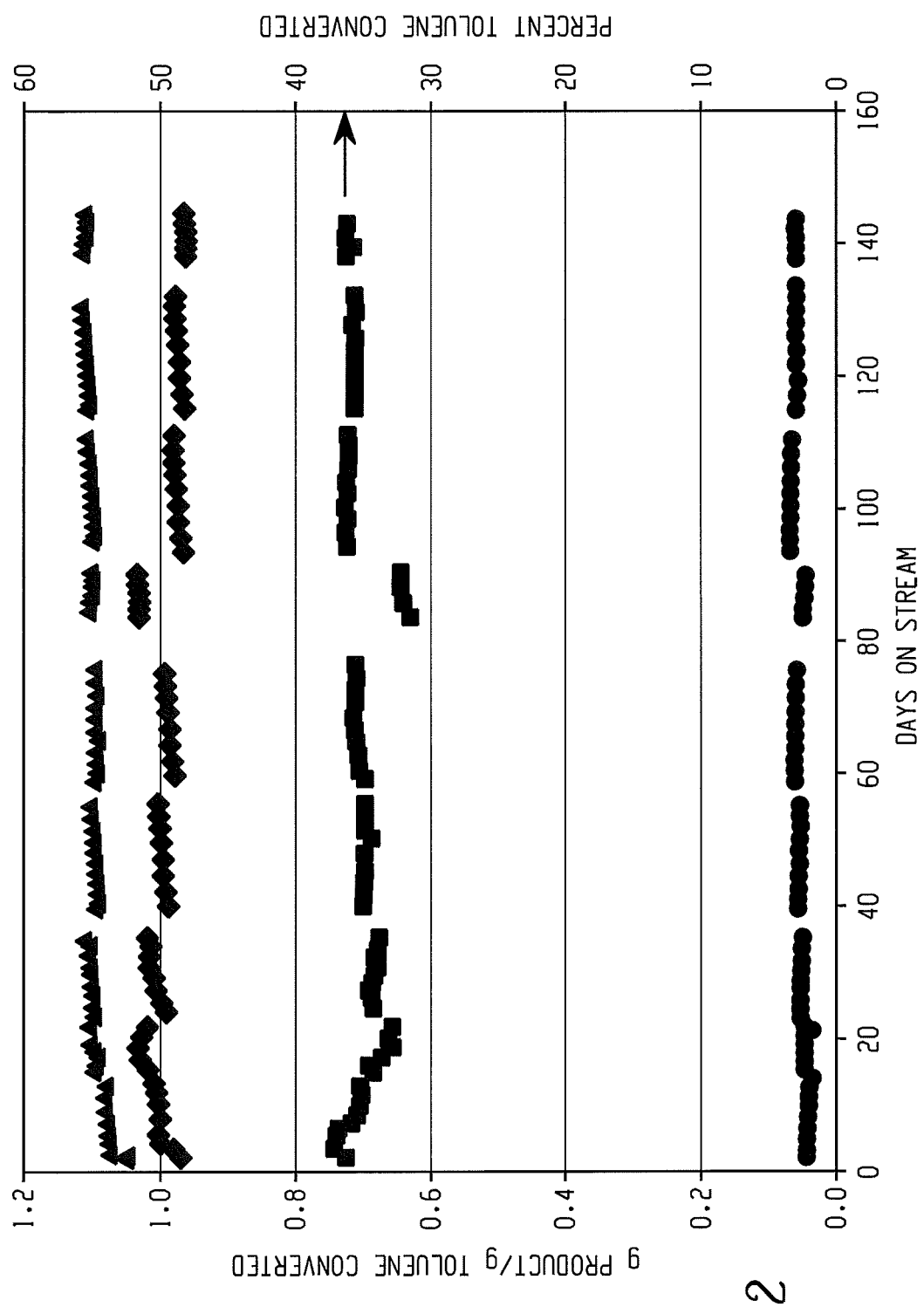
FIG. 2 is a graphical illustration of toluene methylation over the shape selective catalyst of Example 1.

$X_{tol}$ = % toluene conversion,

Tol/MeOH = toluene to methanol molar ratio,

WHSV ($h^{-1}$) based on toluene and methanol feed, $C_{9+}$ Arom = $C_{9+}$ aromatics, The data from Table 3 is plotted in FIG. 2 to show the grams of p-xylene per grams of toluene converted (diamond), the grams of mixed xylene per grams of toluene converted (triangles), the grams of $C_9$ produced per grams of toluene converted (circles), and the toluene conversion (squares) with time on stream. FIG. 2 shows that the catalyst produced 1.09 to 1.11 g of mixed-xylene (of which 0.95 to 1.03 g was p-xylene) and 0.04 to 0.06 g of $C_9$ aromatics (primarily trimethylbenzene and ethyltoluene) per gram of toluene converted at toluene conversion of 34 to 36% over the course of the 143 days the test was run.

Example 3: Toluene Methylation Over Extruded Catalyst B

Extruded catalyst B was used in a toluene methylation reaction with a reactor unit described earlier. In each of the reactors 25 g of 1/16-inch extruded catalyst was loaded. The catalyst was dried and steamed using the same procedure and conditions as described in Example 2. Reaction feed was introduced as follows: hydrogen rate at 4700 sccm, toluene at 350 g/h, steam at 73 g/h, and methanol at 15.8 g/h to the 1$^{st}$ reactor. Additional methanol feed was added to the second and third reactors at 13.7 g/h and 11.5 g/h, respectively. The inlet pressure for all three reactors was adjusted to 52 psig. Catalyst bed temperature was adjusted to 500° C. for each of the three reactors. The catalyst testing continued more than 500 days with multiple catalyst regenerations. The reaction conditions, averaged toluene conversion, and reaction products of mixed xylene, p-xylene, and $C_{9+}$ aromatics for fresh and regenerated catalyst are shown in Table 4, where "catalyst regen" refers to regenerated catalyst.

TABLE 4

| Extruded Catalyst A | | | | | | | | Product, g per g toluene converted | | |
|---|---|---|---|---|---|---|---|---|---|---|
| Regeneration No. | Run days | T, °C. | P, psig | Tol/ MeOH | WHSV, $h^{-1}$ | GHSV, $h^{-1}$ | $X_{tol}$ | Mixed xylene | p-xylene | $C_{9+}$ Aromatics |
| Fresh Catalyst | 1-6 | 500 | 50 | 2.9 | 5.2 | 3200 | 21.6 | 1.02 | 0.86 | 0.12 |
| 1 | 9-49 | 500-570 | 50 | 2.9 | 5.1 | 3000 | 23.4 | 1.06 | 0.90 | 0.09 |
| 2 | 53-157 | 500-590 | 50 | 2.9 | 5.6 | 3400 | 21.4 | 1.08 | 0.96 | 0.07 |
| 3 | 160-178 | 550-590 | 50 | 1.6 | 4.0 | 3000 | 32.7 | 1.07 | 0.92 | 0.09 |
| 4 | 200-215 | 600 | 50 | 1.6 | 4.0 | 3000 | 38.0 | 1.09 | 0.95 | 0.06 |
| 5 | 219-233 | 550 | 50 | 1.4 | 2.3 | 2500 | 38.5 | 1.08 | 0.91 | 0.07 |
| 6 | 240-248 | 550-590 | 50 | 1.9 | 5.9 | 3850 | 30.7 | 1.09 | 0.97 | 0.06 |
| 7 | 251-265 | 550-590 | 50 | 1.9 | 5.9 | 3900 | 30.4 | 1.09 | 0.98 | 0.06 |
| 8 | 270-287 | 550-590 | 50 | 1.5 | 4.0 | 2900 | 36.3 | 1.09 | 0.95 | 0.07 |
| 9 | 292-321 | 550-560 | 50 | 1.5 | 2.0 | 2250 | 39.1 | 1.08 | 0.91 | 0.08 |
| 10 | 326-356 | 550-570 | 50 | 1.5 | 2.5 | 2250 | 38.4 | 1.08 | 0.92 | 0.07 |
| 11 | 362-380 | 550-580 | 50 | 1.5 | 3.1 | 2350 | 38.3 | 1.08 | 0.92 | 0.08 |
| 12* | 385-398 | 550-600 | 50 | | | | 41.8 | 1.16 | 0.96 | 0.09 |
| 13* | 411-425 | 550-600 | 50 | | | | 41.8 | 1.17 | 0.96 | 0.09 |
| 14 | 427-433 | 550-580 | 50 | 1.5 | 4.0 | 2800 | 35.5 | 1.11 | 0.94 | 0.08 |
| 15* | 436-449 | 550-600 | 50 | | | | 41.7 | 1.16 | 0.96 | 0.09 |
| 16 | 452-458 | 550-580 | 50 | 1.5 | 4.0 | 2800 | 35.5 | 1.09 | 0.92 | 0.08 |
| 17 | 460-463 | 550-600 | 50 | 1.3 | 6.9 | 4000 | 32.9 | 1.09 | 0.95 | 0.08 |
| 18 | 468-475 | 550-600 | 50 | 1.3 | 6.9 | 4100 | 34.9 | 1.09 | 0.95 | 0.08 |
| 19 | 479-486 | 550-600 | 50 | 1.3 | 6.9 | 4100 | 34.1 | 1.09 | 0.95 | 0.08 |
| 20 | 490-497 | 550-600 | 50 | 1.3 | 6.9 | 4100 | 33.6 | 1.09 | 0.95 | 0.08 |
| 21 | 501-508 | 550-600 | 50 | 1.3 | 6.9 | 4100 | 33.4 | 1.09 | 0.95 | 0.08 |
| 22 | 512-525 | 550-600 | 50 | 1.5 | 4.0 | 2800 | 35.8 | 1.09 | 0.92 | 0.07 |
| 23 | 533-542 | 550-600 | 50 | 1.5 | 4.0 | 2800 | 35.1 | 1.09 | 0.93 | 0.07 |

All data presented in table are averaged during the period.
$X_{tol}$ = % toluene conversion,
Tol/MeOH = toluene to methanol molar ratio,
WHSV ($h^{-1}$) based on toluene and methanol feed,
$C_{9+}$ Arom = $C_{9+}$ aromatics,
*Tested using toluene feed containing $C_{8-9}$ aromatics (mixed xylene, trimethylbenzene and ethyltoluene)

Figure 3:
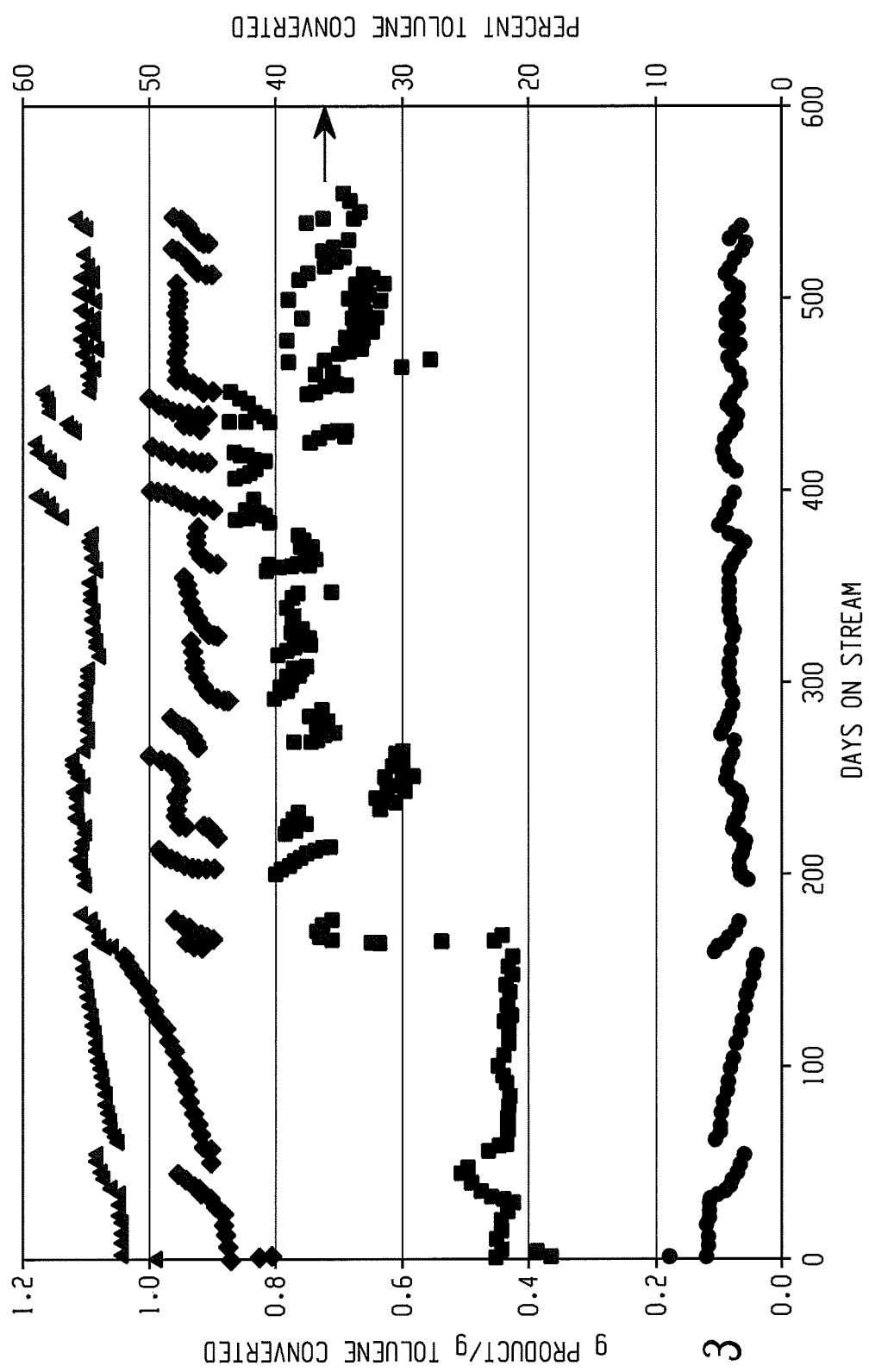
FIG. 3 is a graphical illustration of toluene methylation over the shape selective catalyst of Example 2.

The data from Table 4 is plotted in FIG. 3 to show the grams of p-xylene per grams of toluene converted (diamonds), the grams of mixed xylene per grams of toluene converted (triangles), the grams of $C_9$ produced per grams of toluene converted (circles), and the toluene conversion (squares) with time on stream. FIG. 3 shows that the shape selective catalyst produced 1.04 to 1.17 g of mixed-xylene (of which 0.86 to 1.05 g of p-xylene), and 0.05 to 0.12 g of $C_{9+}$ (primarily trimethylbenzene and ethyltoluene) per gram of toluene feed at toluene conversion of 22 to 43% during about 540 days test run.

Examples 4-9

Examples 4-9 are simulations of the method of making mixed xylene using the process as illustrated in FIG. 1. The simulations were run on Aspen™ Simulation Software, where the compositions of various streams are described in Tables 5-10 for Examples 4-9, respectively, and where a summary of the simulations is shown in Table 11.

Example 4: Toluene Methylation (with No Transalkylation) Using Conditions for Low $C_{9+}$ Production An Aspen simulation was run on by setting the fresh toluene feed (toluene stream 3) to 49500 kg/h, the make-up water (water stream 7) to 0 kg/h, the make-up hydrogen (hydrogen stream 1) to 1798 kg/h, and the fresh methanol feed (methanol stream 11) to 24951 kg/h. Toluene and methanol feeds to alkylation reactor were 230794 kg/h and 26856 kg/h, respectively. Toluene conversion in the alkylation reactor was about 21%, and the mixed xylene selectivity was about 96 mol %. The mixed xylene produced in the toluene alkylation reactor 32 was 1.12 kg per kg of toluene converted (p-isomer of mixed xylene was about 91%). Recovery of toluene in unit 37 and mixed xylene in unit 39 was greater than 99.9%. The purified toluene stream 24 was not routed to the transalkylation reactor 38 as the transalkylation reactor was not used in this simulation. The $C_9$ separation column 40 was also not used in this simulation. The compositions of streams 1, 3, 10, 11, 16, 17, 19, 20, 21, 25, and 26 are shown in Table 5.

TABLE 5

| | Stream Name | | | | | | | | | | |
|---|---|---|---|---|---|---|---|---|---|---|---|
| | $H_2$ Stream | Toluene Stream | Methanol Stream | Alkylation Stream | Alkylated Stream | $C_9$ Stream | $C_{10+}$ Stream | $C_{9+}$ Stream | Transalkylation Stream | Transalkylated Stream | $C_8$ Product Stream |
| | | | | | | Stream No | | | | | |
| Mass Flow | 1 kg/h | 3 kg/h | 11 kg/h | 25 kg/h | 10 kg/h | 20 kg/h | 21 kg/h | 16 kg/h | 26 kg/h | 17 kg/h | 19 kg/h |
| $H_2$ | 1798 | 0 | 0 | 17771 | 17747 | 0 | 0 | 0 | 0 | 0 | 0 |
| $H_2O$ | 0 | 0 | 0 | 46159 | 60130 | 0 | 0 | 0 | 0 | 0 | 0 |

TABLE 5-continued

| | H$_2$ Stream | Toluene Stream | Methanol Stream | Alkylation Stream | Alkylated Stream | C$_9$ Stream | C$_{10+}$ Stream | C$_{9+}$ Stream | Transalkylation Stream | Transalkylated Stream | C$_8$ Product Stream |
|---|---|---|---|---|---|---|---|---|---|---|---|
| Stream No | 1 | 3 | 11 | 25 | 10 | 20 | 21 | 16 | 26 | 17 | 19 |
| Mass Flow | kg/h | kg/h | kg/h | kg/h | kg/h | kg/h | kg/h | kg/h | kg/h | kg/h | kg/h |
| CH$_4$ | 0 | 0 | 0 | 1617 | 1796 | 0 | 0 | 0 | 0 | 0 | 0 |
| Methanol | 0 | 0 | 24951 | 26856 | 2007 | 0 | 0 | 0 | 0 | 0 | 0 |
| C$_2$H$_4$ | 0 | 0 | 0 | 18818 | 20840 | 0 | 0 | 0 | 0 | 0 | 0 |
| C$_2$H$_6$ | 0 | 0 | 0 | 154 | 170 | 0 | 0 | 0 | 0 | 0 | 0 |
| Propene | 0 | 0 | 0 | 8478 | 9356 | 0 | 0 | 0 | 0 | 0 | 0 |
| Propane | 0 | 0 | 0 | 0 | 0 | 0 | 0 | 0 | 0 | 0 | 0 |
| Butene | 0 | 0 | 0 | 1061 | 1154 | 0 | 0 | 0 | 0 | 0 | 0 |
| Benzene | 0 | 0 | 0 | 149 | 151 | 0 | 0 | 0 | 0 | 0 | 0 |
| Toluene | 0 | 49500 | 0 | 230794 | 181683 | 0 | 0 | 0 | 0 | 0 | 5 |
| Ethylbenzene | 0 | 0 | 0 | 0 | 0 | 0 | 0 | 0 | 0 | 0 | 0 |
| o-xylene | 0 | 0 | 0 | 12 | 1327 | 0 | 0 | 0 | 0 | 0 | 1315 |
| m-xylene | 0 | 0 | 0 | 570 | 3485 | 0 | 0 | 0 | 0 | 0 | 2914 |
| p-xylene | 0 | 0 | 0 | 93 | 50647 | 0 | 0 | 0 | 0 | 0 | 50545 |
| 1,2,4-trimethyl benzene | 0 | 0 | 0 | 0 | 1300 | 1299 | 0 | 0 | 0 | 0 | 1 |
| 1-methyl-4-ethylbenzene | 0 | 0 | 0 | 0 | 739 | 737 | 0 | 0 | 0 | 0 | 1 |
| C$_{10}$ aromatics | 0 | 0 | 0 | 0 | 0 | 0 | 0 | 0 | 0 | 0 | 0 |

Example 5: Toluene Methylation with Transalkylation Using Conditions for Low C$_{9+}$ Production; without Imported C$_{9+}$ The Aspen simulation of Example 4 was run except that C$_{9+}$ aromatics produced in the alkylation reactor was fed to the transalkylation reactor. Also, a portion of the purified toluene stream 24 as separated toluene stream 15 was routed to the transalkylation reactor 38 and the remaining portion was recycled as toluene recycle stream 6. Separated toluene stream 15 was combined with C$_9$ stream 20 as transalkylation stream 26. Fresh toluene feed (toluene stream 3) to 49500 kg/h, the make-up water (water stream 7) to 0 kg/h, the make-up hydrogen (hydrogen stream 1) to 1746 kg/h, and the fresh methanol feed (methanol stream 11) to 24226 kg/h. Toluene and methanol feeds to alkylation reactor were 224082 kg/h and 26075 kg/h, respectively. Toluene conversion in the alkylation reactor was about 21% resulting in mixed xylene production of 53191 kg/h (p-isomer of mixed xylene was about 91%). The C$_{9+}$ aromatics produced (kg/h) were transalkylated with toluene producing additional 3318 kg/h mixed xylene. The compositions of streams 1, 3, 10, 11, 16, 17, 19, 20, 21, 25, and 26 are shown in Table 6.

TABLE 6

| | H$_2$ Stream | Toluene Stream | Methanol Stream | Alkylation Stream | Alkylated Stream | C$_9$ Stream | C$_{10+}$ Stream | C$_{9+}$ Stream | Transalkylation Stream | Transalkylated Stream | C$_8$ Product Stream |
|---|---|---|---|---|---|---|---|---|---|---|---|
| Stream No | 1 | 3 | 11 | 25 | 10 | 20 | 21 | 16 | 26 | 17 | 19 |
| Mass Flow | kg/h | kg/h | kg/h | kg/h | kg/h | kg/h | kg/h | kg/h | kg/h | kg/h | kg/h |
| H$_2$ | 1746 | 0 | 0 | 17254 | 17231 | 0 | 0 | 0 | 0 | 0 | 0 |
| H$_2$O | 0 | 0 | 0 | 44817 | 58381 | 0 | 0 | 0 | 2 | 2 | 0 |
| CH$_4$ | 0 | 0 | 0 | 1569 | 1744 | 0 | 0 | 0 | 0 | 0 | 0 |
| Methanol | 0 | 0 | 24226 | 26075 | 1949 | 0 | 0 | 0 | 2 | 2 | 0 |
| C$_2$H$_4$ | 0 | 0 | 0 | 18265 | 20228 | 0 | 0 | 0 | 5 | 5 | 0 |
| C$_2$H$_6$ | 0 | 0 | 0 | 149 | 165 | 0 | 0 | 0 | 0 | 0 | 0 |
| Propene | 0 | 0 | 0 | 8228 | 9080 | 0 | 0 | 0 | 5 | 5 | 0 |
| Propane | 0 | 0 | 0 | 0 | 0 | 0 | 0 | 0 | 0 | 0 | 0 |
| Butene | 0 | 0 | 0 | 1030 | 1119 | 0 | 0 | 0 | 2 | 2 | 0 |
| Benzene | 0 | 0 | 0 | 145 | 146 | 0 | 0 | 0 | 1 | 1 | 0 |
| Toluene | 0 | 49500 | 0 | 224082 | 176400 | 0 | 0 | 0 | 1676 | 236 | 4 |
| Ethylbenzene | 0 | 0 | 0 | 0 | 0 | 0 | 0 | 0 | 0 | 0 | 0 |
| o-xylene | 0 | 0 | 0 | 13 | 1290 | 0 | 0 | 0 | 0 | 0 | 1277 |
| m-xylene | 0 | 0 | 0 | 606 | 3436 | 0 | 0 | 0 | 6 | 6 | 2830 |
| p-xylene | 0 | 0 | 0 | 93 | 49176 | 0 | 0 | 0 | 0 | 3318 | 52393 |
| 1,2,4-trimethyl benzene | 0 | 0 | 0 | 0 | 1263 | 0 | 61 | 0 | 2995 | 1797 | 3 |
| 1-methyl-4-ethylbenzene | 0 | 0 | 0 | 0 | 717 | 0 | 35 | 0 | 1701 | 1020 | 2 |
| C$_{10}$ aromatics | 0 | 0 | 0 | 0 | 0 | 0 | 0 | 0 | 0 | 0 | 0 |

Example 6: Toluene Methylation with Transalkylation Using Conditions for Low $C_{9+}$ Production; with Imported $C_{9+}$ Stream The Aspen simulation of Example 5 was run except additional $C_{9+}$ aromatics ($C_{9+}$ stream 16) was imported and was fed to the transalkylation reactor. Separated toluene stream 15 was combined with $C_9$ stream 20 as transalkylation stream 26. Fresh toluene feed (toluene stream 3) to 49500 kg/h, the make-up water (water stream 7) to 0 kg/h, the make-up hydrogen (hydrogen stream 1) to 1628 kg/h, and the fresh methanol feed (methanol stream 11) to 22588 kg/h. Toluene and methanol feeds to alkylation reactor were 208932 kg/h and 24312 kg/h, respectively. Toluene conversion in the alkylation reactor was about 21% resulting in mixed xylene production of 49595 kg/h (p-isomer of mixed xylene was about 91%). The $C_{9+}$ aromatics produced in the alkylation reactor and imported $C_{9+}$ were transalkylated with toluene producing additional 10801 kg/h mixed xylene. The compositions of streams 1, 3, 10, 11, 16, 17, 19, 20, 21, 25, and 26 are shown in Table 7.

Example 7: Toluene Methylation (with No Transalkylation) Using Conditions for Increased $C_{9+}$ Production The Aspen simulation was run on by setting the fresh toluene feed (toluene stream 3) to 49500 kg/h, the make-up water (water stream 7) 0 kg/h, the make-up hydrogen (hydrogen stream 1) to 1123 kg/h, and the fresh methanol (methanol stream 11) 29290 kg/h. Toluene and methanol feeds to alkylation reactor were 117973 kg/h and 31702 kg/h, respectively. Toluene conversion in the alkylation reactor was about 42% resulting in mixed xylene production of 52091 kg/h. The mixed xylene produced in the toluene alkylation reactor was 1.05 kg per kg toluene converted (p-isomer of mixed xylene was greater than 83%). The $C_{9+}$ aromatics produced in the alkylation reactor and the purified toluene stream 24 was not routed to the transalkylation reactor 38 as the transalkylation reactor was not used in this simulation. The $C_9$ separation column 40 was also not used in this simulation. Recovery of toluene in unit 37 and mixed xylene in unit 39 was greater than 99.9%. The compositions of streams 1, 3, 10, 11, 16, 17, 19, 20, 21, 25, and 26 are shown in Table 8.

TABLE 7

| | $H_2$ Stream | Toluene Stream | Methanol Stream | Alkylation Stream | Alkylated Stream | $C_9$ Stream | $C_{10+}$ Stream | $C_{9+}$ Stream | Transalkylation Stream | Transalkylated Stream | $C_8$ Product Stream |
|---|---|---|---|---|---|---|---|---|---|---|---|
| Stream No | 1 | 3 | 11 | 25 | 10 | 20 | 21 | 16 | 26 | 17 | 19 |
| Mass Flow | kg/h | kg/h | kg/h | kg/h | kg/h | kg/h | kg/h | kg/h | kg/h | kg/h | kg/h |
| $H_2$ | 1628 | 0 | 0 | 16088 | 16066 | 0 | 0 | 0 | 0 | 0 | 0 |
| $H_2O$ | 0 | 0 | 0 | 41787 | 54434 | 0 | 0 | 0 | 7 | 7 | 0 |
| $CH_4$ | 0 | 0 | 0 | 1464 | 1626 | 0 | 0 | 0 | 0 | 0 | 0 |
| Methanol | 0 | 0 | 22588 | 24312 | 1817 | 0 | 0 | 0 | 6 | 6 | 0 |
| $C_2H_4$ | 0 | 0 | 0 | 17037 | 18867 | 0 | 0 | 0 | 17 | 17 | 0 |
| $C_2H_6$ | 0 | 0 | 0 | 139 | 154 | 0 | 0 | 0 | 0 | 0 | 0 |
| Propene | 0 | 0 | 0 | 7675 | 8470 | 0 | 0 | 0 | 17 | 17 | 0 |
| Propane | 0 | 0 | 0 | 0 | 0 | 0 | 0 | 0 | 0 | 0 | 0 |
| Butene | 0 | 0 | 0 | 961 | 1045 | 0 | 0 | 0 | 7 | 7 | 0 |
| Benzene | 0 | 0 | 0 | 135 | 136 | 0 | 0 | 0 | 4 | 4 | 0 |
| Toluene | 0 | 49500 | 0 | 208932 | 164474 | 0 | 0 | 0 | 5416 | 729 | 4 |
| Ethylbenzene | 0 | 0 | 0 | 0 | 0 | 0 | 0 | 25 | 25 | 25 | 25 |
| o-xylene | 0 | 0 | 0 | 15 | 1206 | 0 | 0 | 3 | 3 | 3 | 1193 |
| m-xylene | 0 | 0 | 0 | 683 | 3322 | 0 | 0 | 3 | 26 | 26 | 2641 |
| p-xylene | 0 | 0 | 0 | 95 | 45860 | 0 | 0 | 20 | 21 | 10821 | 56577 |
| 1,2,4-trimethyl benzene | 0 | 0 | 0 | 0 | 1177 | 0 | 188 | 4500 | 13699 | 8220 | 9 |
| 1-methyl-4-ethylbenzene | 0 | 0 | 0 | 0 | 669 | 0 | 32 | 0 | 1586 | 951 | 2 |
| $C_{10}$ aromatics | 0 | 0 | 0 | 0 | 0 | 0 | 450 | 450 | 450 | 450 | 0 |

TABLE 8

| | Stream Name | | | | | | | | | | |
|---|---|---|---|---|---|---|---|---|---|---|---|
| | $H_2$ Stream | Toluene Stream | Methanol Stream | Alkylation Stream | Alkylated Stream | $C_9$ Stream | $C_{10+}$ Stream | $C_{9+}$ Stream | Transalkylation Stream | Transalkylated Stream | $C_8$ Product Stream |
| | Stream No | | | | | | | | | | |
| Mass Flow | 1 kg/h | 3 kg/h | 11 kg/h | 25 kg/h | 10 kg/h | 20 kg/h | 21 kg/h | 16 kg/h | 26 kg/h | 17 kg/h | 19 kg/h |
| $H_2$ | 1123 | 0 | 0 | 10360 | 10265 | 0 | 0 | 0 | 0 | 0 | 0 |
| $H_2O$ | 0 | 0 | 0 | 29986 | 46450 | 0 | 0 | 0 | 0 | 0 | 0 |
| $CH_4$ | 0 | 0 | 0 | 1413 | 1571 | 0 | 0 | 0 | 0 | 0 | 0 |
| Methanol | 0 | 0 | 29290 | 31702 | 2419 | 0 | 0 | 0 | 0 | 0 | 0 |
| $C_2H_4$ | 0 | 0 | 0 | 10572 | 11675 | 0 | 0 | 0 | 0 | 0 | 0 |
| $C_2H_6$ | 0 | 0 | 0 | 1622 | 1788 | 0 | 0 | 0 | 0 | 0 | 0 |
| Propene | 0 | 0 | 0 | 6332 | 6915 | 0 | 0 | 0 | 0 | 0 | 0 |
| Propane | 0 | 0 | 0 | 16238 | 17647 | 0 | 0 | 0 | 0 | 0 | 0 |
| Butene | 0 | 0 | 0 | 27238 | 28587 | 0 | 0 | 0 | 0 | 0 | 0 |
| Benzene | 0 | 0 | 0 | 11356 | 11404 | 0 | 0 | 0 | 0 | 0 | 0 |
| Toluene | 0 | 49500 | 0 | 117973 | 68531 | 0 | 0 | 0 | 0 | 0 | 12 |
| Ethylbenzene | 0 | 0 | 0 | 0 | 0 | 0 | 0 | 0 | 0 | 0 | 0 |
| o-xylene | 0 | 0 | 0 | 114 | 3071 | 7 | 0 | 0 | 0 | 0 | 2950 |
| m-xylene | 0 | 0 | 0 | 475 | 6152 | 2 | 0 | 0 | 0 | 0 | 5675 |
| p-xylene | 0 | 0 | 0 | 2345 | 45802 | 10 | 0 | 0 | 0 | 0 | 43444 |
| 1,2,4-trimethyl benzene | 0 | 0 | 0 | 48 | 3624 | 3576 | 0 | 0 | 0 | 0 | 0 |
| 1-methyl-4-ethylbenzene | 0 | 0 | 0 | 208 | 2080 | 1854 | 0 | 0 | 0 | 0 | 18 |
| $C_{10}$ aromatics | 0 | 0 | 0 | 0 | 0 | 0 | 0 | 0 | 0 | 0 | 0 |

Example 8: Toluene Methylation with Transalkylation Using Conditions for Increased $C_{9+}$ Production; without Imported $C_{9+}$ The Aspen simulation of Example 7 was run except that separated toluene stream 15 (which is fraction of toluene stream 24) was routed to the transalkylation reactor 38. The $C_9$ aromatics ($C_9$ stream 20) produced in toluene methylation reactor was added to the transalkylation reactor 38. The simulation was run with fresh toluene feed (toluene stream 3) 49500 kg/h, the make-up water (water stream 7) 0 kg/h, the make-up hydrogen (hydrogen stream 1) 1038 kg/h, and the fresh methanol feed (methanol stream 11) 27076 kg/h. Toluene and methanol feeds to alkylation reactor were 109056 kg/h and 29306 kg/h, respectively. Toluene conversion in the alkylation reactor was about 42% resulting in mixed xylene production of 48154 kg/h (p-isomer of mixed xylene was about 83%). The $C_{9+}$ aromatics produced (kg/h) were transalkylated with toluene producing additional 8618 kg/h mixed xylene. The compositions of streams 1, 3, 10, 11, 16, 17, 19, 20, 21, 25, and 26 are shown in Table 9.

TABLE 9

| | Stream Name | | | | | | | | | | |
|---|---|---|---|---|---|---|---|---|---|---|---|
| | $H_2$ Stream | Toluene Stream | Methanol Stream | Alkylation Stream | Alkylated Stream | $C_9$ Stream | $C_{10+}$ Stream | $C_{9+}$ Stream | Transalkylation Stream | Transalkylated Stream | $C_8$ Product Stream |
| | Stream No | | | | | | | | | | |
| Mass Flow | 1 kg/h | 3 kg/h | 11 kg/h | 25 kg/h | 10 kg/h | 20 kg/h | 21 kg/h | 16 kg/h | 26 kg/h | 17 kg/h | 19 kg/h |
| $H_2$ | 1038 | 0 | 0 | 9577 | 9489 | 0 | 0 | 0 | 0 | 0 | 0 |
| $H_2O$ | 0 | 0 | 0 | 27719 | 42939 | 0 | 0 | 0 | 29 | 29 | 0 |
| $CH_4$ | 0 | 0 | 0 | 1306 | 1451 | 0 | 0 | 0 | 0 | 0 | 0 |
| Methanol | 0 | 0 | 27076 | 29306 | 2236 | 0 | 0 | 0 | 22 | 22 | 0 |
| $C_2H_4$ | 0 | 0 | 0 | 9773 | 10793 | 0 | 0 | 0 | 15 | 15 | 0 |
| $C_2H_6$ | 0 | 0 | 0 | 1500 | 1653 | 0 | 0 | 0 | 3 | 3 | 0 |
| Propene | 0 | 0 | 0 | 5854 | 6392 | 0 | 0 | 0 | 21 | 21 | 0 |
| Propane | 0 | 0 | 0 | 15040 | 16343 | 0 | 0 | 0 | 66 | 66 | 0 |
| Butene | 0 | 0 | 0 | 25396 | 26643 | 0 | 0 | 0 | 302 | 302 | 0 |
| Benzene | 0 | 0 | 0 | 11242 | 11286 | 0 | 0 | 0 | 634 | 634 | 0 |
| Toluene | 0 | 49500 | 0 | 109056 | 63351 | 0 | 0 | 0 | 4194 | 454 | 14 |
| Ethylbenzene | 0 | 0 | 0 | 0 | 0 | 0 | 0 | 0 | 0 | 0 | 0 |
| o-xylene | 0 | 0 | 0 | 104 | 2838 | 0 | 0 | 0 | 11 | 11 | 2734 |
| m-xylene | 0 | 0 | 0 | 393 | 5641 | 0 | 0 | 0 | 12 | 12 | 5248 |
| p-xylene | 0 | 0 | 0 | 2154 | 42326 | 0 | 0 | 0 | 25 | 8643 | 48788 |
| 1,2,4-trimethyl benzene | 0 | 0 | 0 | 44 | 3350 | 1 | 113 | 0 | 7979 | 4788 | 0 |
| 1-methyl-4-ethylbenzene | 0 | 0 | 0 | 191 | 1922 | 0 | 10 | 0 | 4216 | 2530 | 34 |
| $C_{10}$ aromatics | 0 | 0 | 0 | 0 | 0 | 0 | 0 | 0 | 0 | 0 | 0 |

Example 9: Toluene Methylation with Transalkylation Using Conditions for Increased $C_{9+}$ Production; with Imported $C_{9+}$ Stream The Aspen simulation of Example 8 was run except that additional $C_{9+}$ aromatics ($C_{9+}$ stream 16) was imported and was added to transalkylation stream 26 and fed to transalkylation reactor 38. Simulation was run with fresh toluene feed (toluene stream 3) 49500 kg/h, the make-up water (water stream 7) 0 kg/h, the make-up hydrogen (hydrogen stream 1) 972 kg/h, and the fresh methanol feed (methanol stream 11) 25370 kg/h. Toluene and methanol feeds to alkylation reactor were 102185 kg/h and 27459 kg/h, respectively. Toluene conversion in the alkylation reactor was about 42% resulting in mixed xylene production of 45120 kg/h (p-isomer of mixed xylene was about 83%). The $C_{9+}$ aromatics produced in the alkylation reactor and imported $C_{9+}$ were transalkylated with toluene producing additional 15253 kg/h mixed xylene. The compositions of streams 1, 3, 10, 11, 16, 17, 19, 20, 21, 25, and 26 are shown in Table 10.

TABLE 10

| | $H_2$ Stream | Toluene Stream | Methanol Stream | Alkylation Stream | Alkylated Stream | $C_9$ Stream | $C_{10+}$ Stream | $C_{9+}$ Stream | Transalkylation Stream | Transalkylated Stream | $C_8$ Product Stream |
|---|---|---|---|---|---|---|---|---|---|---|---|
| Stream No | 1 | 3 | 11 | 25 | 10 | 20 | 21 | 16 | 26 | 17 | 19 |
| Mass Flow | kg/h | kg/h | kg/h | kg/h | kg/h | kg/h | kg/h | kg/h | kg/h | kg/h | kg/h |
| $H_2$ | 972 | 0 | 0 | 8974 | 8891 | 0 | 0 | 0 | 0 | 0 | 0 |
| $H_2O$ | 0 | 0 | 0 | 25973 | 40233 | 0 | 0 | 0 | 58 | 58 | 0 |
| $CH_4$ | 0 | 0 | 0 | 1224 | 1360 | 0 | 0 | 0 | 0 | 0 | 0 |
| Methanol | 0 | 0 | 25370 | 27459 | 2095 | 0 | 0 | 0 | 43 | 43 | 0 |
| $C_2H_4$ | 0 | 0 | 0 | 9152 | 10108 | 0 | 0 | 0 | 30 | 30 | 0 |
| $C_2H_6$ | 0 | 0 | 0 | 1404 | 1548 | 0 | 0 | 0 | 5 | 5 | 0 |
| Propene | 0 | 0 | 0 | 5483 | 5988 | 0 | 0 | 0 | 42 | 42 | 0 |
| Propane | 0 | 0 | 0 | 14074 | 15295 | 0 | 0 | 0 | 130 | 130 | 0 |
| Butene | 0 | 0 | 0 | 23735 | 24904 | 0 | 0 | 0 | 600 | 600 | 0 |
| Benzene | 0 | 0 | 0 | 10494 | 10535 | 0 | 0 | 0 | 1258 | 1258 | 0 |
| Toluene | 0 | 49500 | 0 | 102185 | 59360 | 0 | 0 | 0 | 7809 | 1190 | 16 |
| Ethylbenzene | 0 | 0 | 0 | 0 | 0 | 0 | 0 | 25 | 25 | 25 | 25 |
| o-xylene | 0 | 0 | 0 | 98 | 2659 | 0 | 0 | 3 | 13 | 13 | 2564 |
| m-xylene | 0 | 0 | 0 | 344 | 5261 | 0 | 0 | 3 | 19 | 19 | 4919 |
| p-xylene | 0 | 0 | 0 | 2016 | 39657 | 0 | 0 | 20 | 53 | 15306 | 52912 |
| 1,2,4-trimethyl benzene | 0 | 0 | 0 | 41 | 3139 | 1 | 519 | 4500 | 17692 | 10615 | 1 |
| 1-methyl-4-ethylbenzene | 0 | 0 | 0 | 179 | 1801 | 0 | 29 | 0 | 3893 | 2336 | 36 |
| $C_{10}$ aromatics | 0 | 0 | 0 | 0 | 0 | 0 | 450 | 450 | 821 | 821 | 0 |

A comparison of Examples 4-9 is shown in Table 11 below. Examples 4, 5, and 6 resulted in lower toluene conversion than the Examples 7, 8 and 9. In general, the lower toluene conversion resulted in increased selectivities of both mixed xylene and p-xylene. In order to maintain the comparable production rate for mixed xylene and p-xylene at lower toluene conversions, the size and the capital investment ("capital expenditure", also known as "CAPEX") for the reactors and separation units will be significantly higher than those at the higher toluene conversions (compare Examples 4-6 with 7-9). Combining toluene alkylation with transalkylation results in higher internal rate of return (IRR) due to lower production cost and capital cost (compare Examples 4 and 5 or 6, and Examples 7 and 8 or 9, see Table 11). The benefit of integration of alkylation with transalkylation is particularly significant for increased toluene conversion cases where increased amounts of $C_{9+}$ aromatics are formed.

TABLE 11

| | Example | | | | | |
|---|---|---|---|---|---|---|
| | 4 | 5 | 6 | 7 | 8 | 9 |
| Transalkylation unit | no | yes | yes | no | yes | yes |
| fresh toluene feed (kg/h) | 49500 | 49500 | 49500 | 49500 | 49500 | 49500 |
| fresh methanol feed (kg/h) | 24951 | 24226 | 22588 | 29290 | 27076 | 25370 |
| % toluene conversion in alkylation reactor | 21.3 | 21.3 | 21.3 | 41.9 | 41.9 | 41.9 |
| mol % mixed xylene selectivity for catalyst in alkylation reactor | 96.4 | 96.4 | 96.4 | 90.4 | 90.4 | 90.4 |

TABLE 11-continued

| | Example | | | | | |
|---|---|---|---|---|---|---|
| | 4 | 5 | 6 | 7 | 8 | 9 |
| imported $C_{9+}$ aromatics (kg/h) | 0 | 0 | 5000 | 0 | 0 | 5000 |
| mixed xylene in stream 19 (kg/h) | 54774 | 56500 | 60411 | 52070 | 56770 | 60395 |
| p-xylene in stream 19 (kg/h) | 50545 | 52393 | 56577 | 43444 | 48788 | 52912 |
| mol % p-xylenes in mixed xylene | 91.3 | 91.2 | 91.0 | 83.2 | 83.3 | 83.4 |
| production cost, $/kg mixed xylene | 1.36 | 1.32 | 1.31 | 1.43 | 1.30 | 1.30 |
| CAPEX ($MM) | 192 | 196 | 196 | 134 | 140 | 140 |
| IRR (%) | 23 | 24 | 24 | 28 | 33 | 33 |

Set forth below are examples of the method disclosed here.

Embodiment 1

A method of producing a purified mixed xylene comprising: introducing toluene and methanol to an alkylation reactor; reacting the toluene and the methanol in the alkylation reactor to form a hydrocarbon stream comprising a first mixed xylene, wherein the alkylation reactor comprises an alkylation catalyst; separating the hydrocarbon stream into a toluene stream and a separated $C_{8+}$ stream; introducing the toluene stream to a transalkylation reactor with a transalkylation catalyst to produce a transalkylated stream comprising a second mixed xylene; adding the transalkylated stream to the hydrocarbon stream; and separating a $C_8$ product stream comprising the purified mixed xylene from the separated $C_{8+}$ stream.

Embodiment 2

A method of producing a purified mixed xylene comprising: introducing a toluene stream and methanol to an alkylation reactor, wherein the toluene stream comprises toluene and 0 wt % to 30 wt % of $C_{9+}$ aromatics, based upon a total weight of the toluene stream; reacting the toluene and the methanol in the alkylation reactor to form a hydrocarbon stream comprising a first mixed xylene, wherein the alkylation reactor comprises an alkylation catalyst; separating the hydrocarbon stream into a toluene stream and a separated $C_{8+}$ stream; introducing the toluene stream to a transalkylation reactor with a transalkylation catalyst to produce a transalkylated stream comprising a second mixed xylene; adding the transalkylated stream to the hydrocarbon stream; and separating a $C_8$ product stream comprising the purified mixed xylene from the separated $C_{8+}$ stream.

Embodiment 3

The method of any of Embodiments 1-2, wherein the alkylation catalyst comprises a phosphorus containing, medium pore, pentasil zeolite having a silica/alumina ratio of greater than or equal to 200.

Embodiment 4

The method of Embodiment 3, wherein the phosphorus is present in an amount of 0.01 to 0.15 g per gram of zeolite.

Embodiment 5

The method of any of Embodiments 1-4, wherein the toluene is introduced to the alkylation reactor via a toluene stream comprising 1 wt % to 30 wt % of $C_{9+}$ aromatics, based upon the total weight of the toluene stream.

Embodiment 6

The method of Embodiment 5, wherein the toluene stream comprises 5 wt % to 30 wt % of $C_{9+}$ aromatics.

Embodiment 7

The method of Embodiment 6, wherein the toluene stream comprises 10 wt % to 30 wt % of $C_{9+}$ aromatics.

Embodiment 8

The method of any of Embodiments 1-7, wherein the purified mixed xylene comprises greater than or equal to 85 wt % p-xylene based on the total amount of mixed xylene.

Embodiment 9

The method of any of Embodiments 1-8, wherein the alkylation catalyst has a selectivity for para-xylene of greater than or equal to 80 mol %.

Embodiment 10

The method of any of Embodiments 1-8, wherein the alkylation catalyst has a selectivity for para-xylene of less than or equal to 75 mol %.

Embodiment 11

The method of any of Embodiments 1-10, further comprising separating the $C_{8+}$ stream in a xylene column into the $C_8$ product stream and a separated $C_{9+}$ stream.

Embodiment 12

The method of Embodiment 11, further comprising separating the separated $C_{9+}$ stream in a $C_9$ separation column into a $C_9$ stream and a $C_{10+}$ stream; and introducing the $C_9$ stream to the transalkylation reactor.

Embodiment 13

The method of any of Embodiments 1-12, further comprising introducing a $C_{9+}$ stream to the transalkylation reactor.

Embodiment 14

The method of any of Embodiments 1-13, wherein greater than or equal to 0.05 g of $C_{9+}$ aromatics per gram of toluene converted is produced in the alkylation reactor.

In general, the disclosure may alternately comprise, consist of, or consist essentially of, any appropriate components herein disclosed. The disclosure may additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

All ranges disclosed herein are inclusive of the endpoints, and the endpoints are independently combinable with each other (e.g., ranges of "up to 25 wt %, or, more specifically, 5 to 20 wt %", is inclusive of the endpoints and all intermediate values of the ranges of "5 to 25 wt %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the catalyst(s) includes one or more catalysts). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

All references cited in the above disclosure are incorporated herein in their entirety.

We claim:

1. A method of producing a purified mixed xylene comprising:
   introducing toluene and methanol to an alkylation reactor;
   reacting the toluene and the methanol in the alkylation reactor to form a hydrocarbon stream comprising a first mixed xylene, wherein the alkylation reactor comprises an alkylation catalyst;
   separating the hydrocarbon stream into a toluene stream and a separated $C_{8+}$ stream;
   introducing the toluene stream to a transalkylation reactor with a transalkylation catalyst to produce a transalkylated stream comprising a second mixed xylene;
   adding the transalkylated stream to the hydrocarbon stream; and
   separating a $C_8$ product stream comprising the purified mixed xylene from the separated $C_{8+}$ stream;
   wherein greater than or equal to 0.05 g of $C_{9+}$ aromatics per gram of toluene converted is produced in the alkylation reactor.

2. The method of claim 1, wherein the alkylation catalyst comprises a phosphorus containing, medium pore, pentasil zeolite having a silica/alumina ratio of greater than or equal to 200.

3. The method of claim 2, wherein the phosphorus is present in an amount of 0.01 to 0.15 g per gram of zeolite.

4. The method of claim 2, wherein the phosphorus is present in an amount of 0.07 to 0.15 g per gram of zeolite.

5. The method of claim 1, wherein the alkylation catalyst has a selectivity for para-xylene of greater than or equal to 80 mol %.

6. The method of claim 1, further comprising separating the $C_{8+}$ stream in a xylene column into the $C_8$ product stream and a separated $C_{9+}$ stream.

7. The method of claim 6, further comprising separating the separated $C_{9+}$ stream in a $C_9$ separation column into a $C_9$ stream and a $C_{10+}$ stream; and introducing the $C_9$ stream to the transalkylation reactor.

8. The method of claim 1, further comprising introducing a $C_{9+}$ stream to the transalkylation reactor.

9. A method of producing a purified mixed xylene comprising:
   introducing toluene and methanol to an alkylation reactor;
   reacting the toluene and the methanol in the alkylation reactor to form a hydrocarbon stream comprising a first mixed xylene, wherein the alkylation reactor comprises an alkylation catalyst;
   separating the hydrocarbon stream into a toluene stream and a separated $C_{8+}$ stream;
   introducing the toluene stream to a transalkylation reactor with a transalkylation catalyst to produce a transalkylated stream comprising a second mixed xylene;
   adding the transalkylated stream to the hydrocarbon stream; and
   separating a $C_8$ product stream comprising the purified mixed xylene from the separated $C_{8+}$ stream;
   wherein the purified mixed xylene comprises greater than or equal to 85 wt % p-xylene based on the total amount of mixed xylene.

10. A method of producing a purified mixed xylene comprising:
    introducing toluene and methanol to an alkylation reactor;
    reacting the toluene and the methanol in the alkylation reactor to form a hydrocarbon stream comprising a first mixed xylene, wherein the alkylation reactor comprises an alkylation catalyst;
    separating the hydrocarbon stream into a toluene stream and a separated $C_{8+}$ stream;
    introducing the toluene stream to a transalkylation reactor with a transalkylation catalyst to produce a transalkylated stream comprising a second mixed xylene;
    adding the transalkylated stream to the hydrocarbon stream; and
    separating a $C_8$ product stream comprising the purified mixed xylene from the separated $C_{8+}$ stream;
    wherein the alkylation catalyst has a selectivity for para-xylene of less than or equal to 75 mol %.

* * * * *